(12) United States Patent
Coignet

(10) Patent No.: US 7,449,303 B2
(45) Date of Patent: Nov. 11, 2008

(54) USE OF JAG2 EXPRESSION IN DIAGNOSIS OF PLASMA CELL DISORDERS

(75) Inventor: Lionel J. Coignet, Amherst, NY (US)

(73) Assignee: Health Research, Inc., Buffalo, NY (US)

( * ) Notice: Subject to any disclaimer, the term of this patent is extended or adjusted under 35 U.S.C. 154(b) by 430 days.

(21) Appl. No.: 10/837,722

(22) Filed: May 3, 2004

(65) Prior Publication Data

US 2005/0003406 A1 Jan. 6, 2005

Related U.S. Application Data

(60) Provisional application No. 60/467,733, filed on May 2, 2003.

(51) Int. Cl.
*G01N 33/05* (2006.01)
*G01N 33/58* (2006.01)
*G01N 33/577* (2006.01)
*C12Q 1/68* (2006.01)
*C07K 14/71* (2006.01)
*C07K 16/28* (2006.01)
*C12N 15/12* (2006.01)

(52) U.S. Cl. .................. 435/7.21; 435/6; 536/24.3; 536/23.5; 530/530; 530/350; 530/326; 530/387.1; 530/388.25; 530/391.3

(58) Field of Classification Search .................. None
See application file for complete search history.

(56) References Cited

U.S. PATENT DOCUMENTS 6,136,952 A * 10/2000 Li et al.
6,291,210 B1 9/2001 Sakano et al.
2001/0048930 A1 12/2001 Lamb et al.
2003/0232364 A1 * 12/2003 Shaughnessy et al.

FOREIGN PATENT DOCUMENTS

| WO | WO 00/25809 | 5/2000 |
| WO | WO 03/087159 A2 | 10/2003 |
| WO | WO 03/087159 A3 | 10/2003 |
| WO | WO 2004/076682 A2 | 9/2004 |
| WO | WO 2004/099379 A2 | 11/2004 |

OTHER PUBLICATIONS

De Vos et al., Identifying intercellular signaling genes expressed in malignant plasma cells by using complementary DNA arrays, Blood, 98(3):771-780, Aug. 2001.*

Deng et al., Characterization, chromosomal localization, and the complete 30-kd DNA sequence of the human Jagged2 (JAG@) gene, Genomics, 63(1):133-138, 2000.*

(Continued)

*Primary Examiner*—Lorraine Spector
*Assistant Examiner*—Claire Kaufman
(74) *Attorney, Agent, or Firm*—Hodgson Russ LLP

(57) ABSTRACT

The present invention is based on the finding that plasma cell disorders such as Multiple Myeloma and Monoclonal Gammopathy of Unknown Significance are characterized by an increase in the expression of JAG2. Accordingly, the present invention provides a method for diagnosis of plasma cell disorders by detecting the expression or overexpression of JAG2. The expression or overexpression of JAG2 may be detected as increased mRNA transcripts or increased protein.

22 Claims, 8 Drawing Sheets

OTHER PUBLICATIONS

Hu et al., Profiling of differentially expressed cancer-realted genes in esophageal squamous cell carcinoma (ESCC) using human cancer cDNA arrays: overexpression of oncogene MET correlates with tumor differentiation in ESCC, Clin. Canc. Res., 7:3519-3525, Nov. 2001.*

Gutgemann et al., Isolation of invastion-associated cDNAs in melanoma, Arch. Dermatol. Res. 293:283-290, 2001.*

Gaiger, et al.; Identification of Genes Associated with Multiple Myeloma and Monoclonal Gammopathy of Undetermined Significance Using the Myeloma Microarray; European Journal of Cancer, Pergamon Press; Nov. 21, 2002, vol. 38, Paragraph 344; XP-002383846; p. S103.

Luo, et al.; Isolation and Functional Analysis of a cDNA for Human Jagged2, a Gene Encoding a Ligand for the Notch1 Receptor; Molecular and Cellular Biology, American Society for Microbiology; Washington, US; Oct. 1997; vol. 17, No. 10; XP-000938415; pp. 6057-6067.

Gray, et al.; Human Ligands of the Notch Receptor; American Journal of Pathology; Mar. 1999, vol. 154, No. 3; XP-000960906; pp. 785-794.

Almeida, et al.; Immunophenotypic and DNA Content Characteristics of Plasma Cells in Multiple Myeloma and Monoclonal Gammopathy of Undetermined Significance; Pathologie et Biologie, L'Expansion Scientifique Francaise, Paris, FR; Feb. 1999, vol. 47, No. 2; XP-009067443; pp. 119-127.

Felli, et al.; Expression Pattern of Notch1, 2 and 3 and Jagged1 and 2 in Lymphoid and Stromal Thymus Components; Distinct Ligand—Receptor Interactions in Intrathymic T Cell Development; International Immunology, vol. 11, No. 77; XP-002384016; pp. 1017-1025.

Houde, et al.; Overexpression of the Notch Ligand JAG2 in Malignant Plasma Cells From Multiple Myeloma Patients and Cell Lines; Blood, Dec. 1, 2004, vol. 104, No. 12; XP-002380593; pp. 3697-3704.

Franziska, et al.; Activated Notch signaling might be a novel therapeutic target for multiple myeloma; Database Biosis [online]; Database accession No. PREV200400161099 abstract; Blood, Nov. 16, 2003, vol. 102, No. 11; p. 928a; XP-002454293.

* cited by examiner

USE OF JAG2 EXPRESSION IN DIAGNOSIS OF PLASMA CELL DISORDERS

This application claims priority to U.S. provisional application No. 60/467,733 filed on May 2, 2003, the disclosure of which is incorporated herein by reference.

FIELD OF THE INVENTION

This invention relates generally to the field of plasma cell disorder and more particularly provides a method for the diagnosis of plasma cell disorders.

BACKGROUND OF THE INVENTION

Multiple myeloma (MM) is the second most frequent blood disorder in the United States. Some 13,000 new cases are diagnosed each year. MM is a clonal plasma cell proliferative disease that affects terminally differentiated B cells (i.e. plasma cells). It accounts for 10% of all malignant hematologic neoplasms. Despite some advances in chemotherapeutic regimens, this disease remains incurable, with a median survival for MM patients of 40 months. Like MM, Monoclonal Gammopathy of Unknown Significance (MGUS) is characterized by monoclonal immunoglobulin in the serum and urine and an increase of monoclonal plasma cells in the bone marrow. However, MGUS patients do not suffer from the clinical manifestations of MM. Importantly, 25% of patients with MGUS progress to myeloma.

Detection of neoplastic plasma cells in the marrow is central to making the diagnosis of multiple myeloma and distinguishes the disease from other conditions associated with a paraprotein. The neoplastic cells produce immunoglobulin light chain of only one type, allowing discrimination between a monoclonal and polyclonal increase in bone marrow plasma cells by immunocytology (McLennan et al, Brit. Med. J., vol. 308: pp1033-1036, 1994). A monoclonal immunoglobulin band (paraprotein) is found in the blood or urine, or both in 98% of patients with multiple myeloma. The remaining 2% of patients have non-secretory disease (Kyle et al, Stem Cells. vol 2, pp56-60, 1995). Finding a paraprotein supports but does not make the diagnosis of multiple myeloma. The serum paraprotein may be of any immunoglobulin class other than IgM, which in multiple myeloma occurs only as an extreme rarity. It is important to look for paraproteins both in the blood and in the urine, as intact monoclonal immunoglobulin is detectable in the serum in only 80% of patients. A similar proportion of patients have excess monoclonal free light chain in the urine. Serial measurements of blood and urine paraprotein concentrations provide a useful guide to indicate a plasma cell disorder, response to treatment, stability of the disease, and the onset of disease progression.

Several other markers can be considered in multiple myeloma, not for diagnostic but as prognostic factors. These parameters include: plasma cell labeling index, beta2-microglobulin, cytogenetic abnormalities, plasma blastic morphology, interleukin-6, LDH, angiogenesis, immunphenotyping, DNA aneuploidy, activated oncogenes, and other factors (reviewed in Rajkumar & Greipp, 1999 pp 1295-1315 in Hematology/Oncology clinics of North America, Kyle and Gertz, editors. Monoclonal Gammopathies and related disorders. W B Sabders editions).

Even though detection of increased numbers of plasma cells in the marrow is indicative in many cases of plasma cell disorder, this does not exclude the occurrence of such a phenomenon due to infection or other idiopathic causes as would a method which provided information about the cause of the proliferation itself, such as altered expression of a gene involved in regulating cell proliferation. Thus, there is a need for a method of diagnosis of plasma cell disorder that can detect altered gene expression associated with the plasma cell proliferation indicative of MGUS and MM.

SUMMARY OF THE INVENTION

The present invention provides compositions and methods for detection of plasma cell disorders. The present method is based on the observations that Jagged 2 (JAG2) expression is increased in MM cell lines as well as in primary tumors obtained from patients diagnosed with plasma cell disorders including MM or MGUS, but not with patients with other hematologic neoplasms or non-hematologic neoplasms.

In one embodiment of the invention, a method is provided to determine the expression of JAG2 in bone marrow samples obtained from patients. The expression of JAG2 may be evaluated by determining the levels of JAG2 mRNA or the levels of JAG2 protein. Methods for determination of levels of JAG2 mRNA include, but are not limited to, Northern blotting, oligonucleotide hybridization, PCR based techniques and in situ hybridization techniques. Methods for determination of JAG2 protein levels include, but are not limited to, immunoassays such as enzyme linked immunosorbent assays (ELISAs), immunofluorescence based techniques and FACS based techniques.

Compositions are also provided for determination of JAG2 mRNA or protein. The compositions include primers useful for PCR amplification of reverse transcribed mRNA and antibodies including polyclonal and monoclonal antibodies for the detection of JAG2 protein.

DETAILED DESCRIPTION OF THE INVENTION

The present invention is based on the unexpected finding that the expression of JAG2 is increased in plasma cell disorders. The term "plasma cell disorder" as used herein refers to a proliferative disorder of the plasma cells that is characterized by monoclonal IgG or IgM in the serum or urine and an increase in monoclonal plasma cells in the bone marrow. Examples of plasma cell disorders include MGUS, MM, smoldering MM and plasma cell leukemia.

Figure 1:
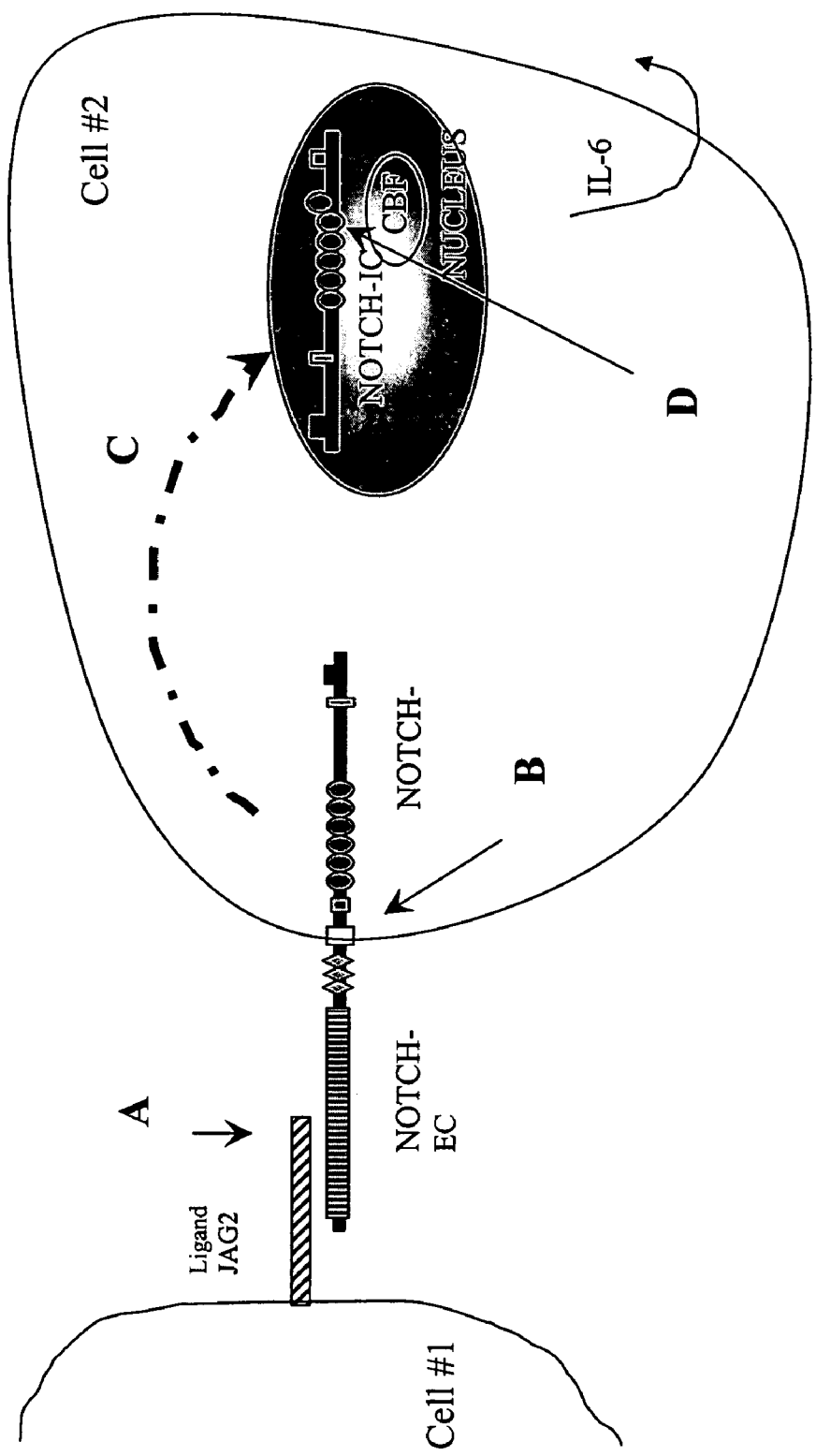
FIG. 1: Schematic representation of the physiological activation of NOTCH, with Cell #1 expressing JAG2 and cell #2 expressing NOTCH. A: JAG2 binds NOTCH via cell-to-cell contact. B: Binding of JAG2 induces a proteolytic cleavage of the intracellular part of NOTCH (NOTCH-IC). C: Once cleaved, NOTCH-IC is translocated into the nucleus. D: Once in the nucleus, NOTCH-IC can bind to downstream effectors such as CBF1, to activate, for example, the IL-6 gene transcription.
Figure 2:
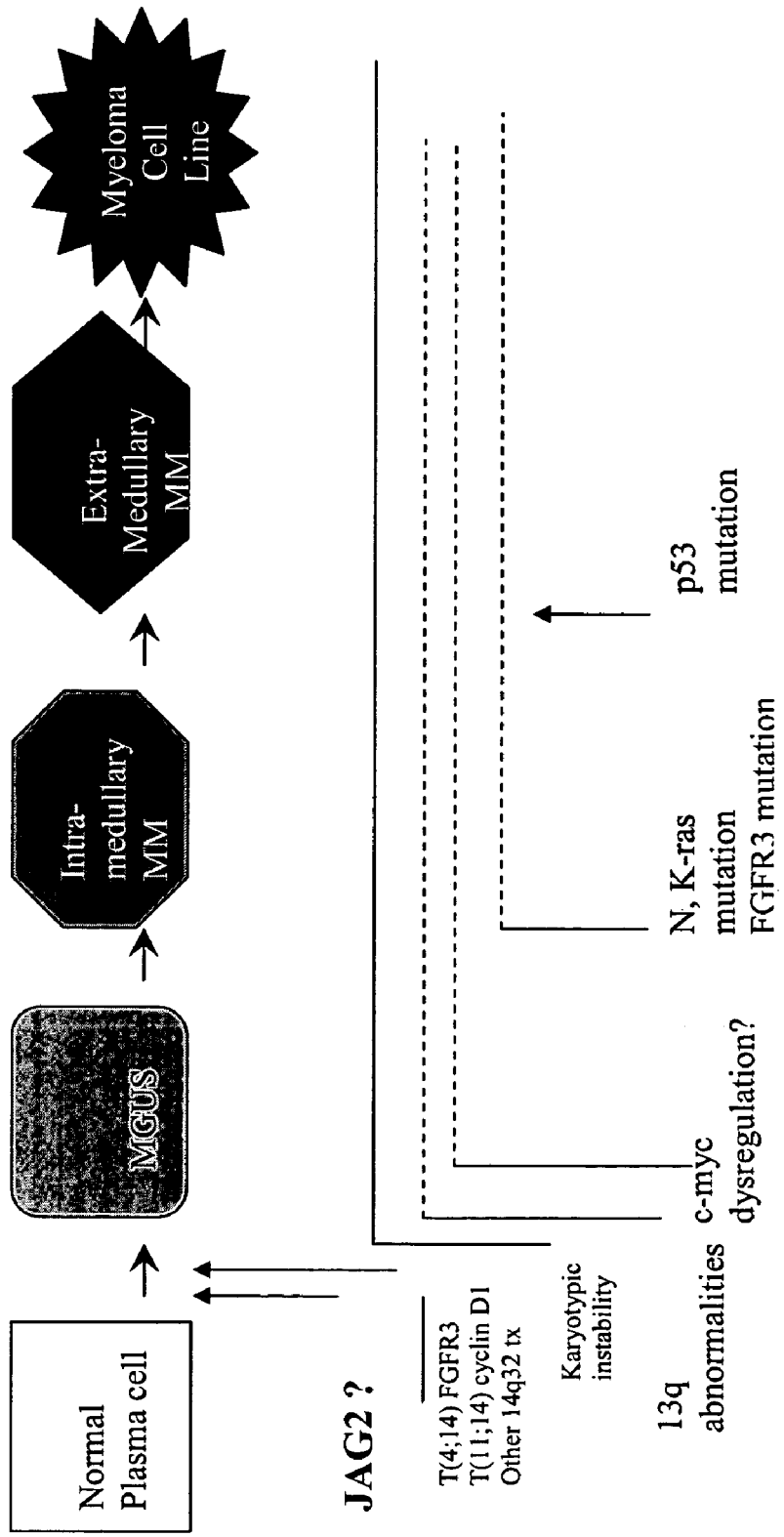
FIG. 2: Progressive genetic events in MM. Although not every stage is discernible in each patient, there appears to be an ordered progression from a normal plasma cell to MGUS where the cells are immortalized, but not transformed and do not progressively accumulate or cause bone destruction; to intra-medullary myeloma, where the cells are confined to the BM micro-environment, accumulate and cause bone destruction; to extra-medullary myeloma, where the cells proliferate more rapidly and grow in the blood (plasma cell leukemia) or other extra-medullary sites; to a myeloma cell line, where the cells may be propagated in vitro. This model summarizes the possible timing of genetic events in relation to clinical progression.

Although not intending to be bound by any particular theory, the proposed effect of expression or over-expression of JAG2 is described in FIG. 1 which illustrates how JAG2 acts. It is considered that the IL-6 gene can be triggered by the NOTCH-1 & -2 genes (which play multiple key roles in cell fate determination) through the CBF1/RBPJ-Kappa pathway. Activated forms of NOTCH-1 & -2 convert CBF1 from a repressor to an activator of transcription. The NOTCH proteins are activated by ligand binding, and one of the ligands for NOTCH-1 and -2 is JAG2. As further described in the Examples presented herein, we have determined that MM cell lines, as well as MGUS/MM patient samples, have altered JAG2 expression both at the messenger and protein levels. Such expression is not observed in plasma cells from a series of normal controls. It is also considered that the deregulation of JAG2 expression is a consequence of hypomethylation of the JAG2 promoter. The altered expression of JAG2 may represent an early event in MGUS/MM pathogenesis (FIG. 2).

Accordingly, the present invention provides compositions and methods for diagnosis of plasma cell disorders by detecting the expression or over-expression of JAG2 in plasma cells. Since the level of JAG2 expression has been found to be negligible in samples of plasma cells obtained from patients that do not have plasma cell disorders (normal patients, patients diagnosed with NHL or breast cancer), in one embodiment, the detection of expression of JAG2 in plasma cell samples is considered to be an indication of a plasma cell disorder. In another embodiment, the expression of JAG2 in a patient sample is compared to the expression in a negative control (such as a normal patient or a patient who does not have a plasma cell disorder). A difference in the expression of JAG2 is termed as "over-expression" which indicates that JAG2 protein or mRNA is expressed at a level higher than in the control.

The term "diagnosis" or "diagnostic test" refers to the identification of the disease at any stage of its development, i.e., it includes the determination whether an individual has the disease or not and/or includes determination of the stage of the disease.

The method comprises the steps of obtaining a sample of the bone marrow which comprises plasma cells, and evaluating the sample for the expression or overexpression of JAG2. The expression or overexpression of JAG2 may be determined by detecting JAG related transcripts such as mRNA or levels of JAG2 protein.

In one embodiment, the determination of the level of expression of JAG2 encompasses the use of nucleic acid sequences such as specific oligonucleotides to detect the presence of mRNA that encodes JAG2 nucleic acid in plasma cell sample. One skilled in the art may use nucleic acid hybridization probes in solution hybridizations or solid-phase procedures. In solid-phase procedures, the test or probe nucleic acid is adsorbed or otherwise affixed to a selected matrix or surface. The fixed, single-stranded nucleic acid is then subjected to specific hybridization with selected probes which are typically labeled with $^{32}$P-nucleotides or nucleotides to which a label, such as biotin, has been covalently conjugated. For example, one may use the well known nucleic acid based microarrays, in which probe nucleic acids are immobilized, to detect the JAG2 mRNA species. Some examples of hybridization methods for detection of expression of JAG mRNA are provided below.

A nucleic acid based method for determining whether a sample contains cells expressing JAG2 is the Northern Blot analysis of mRNA extracted from a sample. The techniques for performing Northern blot analyses are well known to those having ordinary skill in the art and are described in Sambrook, J. et al., (1989) Molecular Cloning: A Laboratory Manual, Cold Spring Harbor Laboratory Press, Cold Spring Harbor, N.Y. mRNA extraction, electrophoretic separation of the mRNA, blotting, probe preparation and hybridization are all well known techniques. Hybridization probes, including oligonucleotide probes for detecting mRNA can easily be made or designed from the known sequence of JAG2 (gene ref. NM145159, at the NCBI database: http://www.ncbi.nlm.nih.gov/entrez). For Northern blotting analysis, the mRNA is extracted using poly dT columns and the material is separated by electrophoresis and transferred to a suitable matrix such as nitrocellulose paper. Labeled probes made from an isolated fragment or fragments can be used to visualize the presence of a complementary fragment fixed to the nitrocellulose paper. Hybridization conditions can be routinely optimized to minimize background signal.

As used herein, the term "oligonucleotide" refers to a nucleic acid, generally of at least 10, preferably at least 15, and more preferably at least 20 nucleotides, preferably no more than 100 nucleotides. Generally, oligonucleotides are prepared synthetically, preferably on a nucleic acid synthesizer. As set forth in the patents noted above, for nucleic acid arrays oligonucleotides can be synthesized in situ. Accordingly, oligonucleotides can be prepared with non-naturally occurring phosphoester analog bonds, such as thioester bonds, etc.

Another method for detecting JAG2 mRNA expression in a sample of fixed plasma cells or a fixed or frozen section of a primary tumor by in situ hybridization. In this technique, labeled hybridization probes are contacted with cells or sections of tissue sample under stringent hybridization conditions. Following removal of non-specific binding, the hybridization of specific probes is detected based on the label.

Another method for detecting mRNA that encodes the JAG2 protein uses polymerase chain reaction (PCR) technology. PCR technology is well known to those skilled in the art. (see Methods for practicing PCR technology are disclosed in "PCR Protocols: A Guide to Methods and Applications", Innis, M. A., et al. Eds. Academic Press, Inc. San Diego, Calif. (1990); and "Polymerase Chain Reaction" Erlich, H. A., et al., Eds. Cold Spring Harbor Press, Cold Spring Harbor, N.Y. (1989). PCR technology allows for the rapid generation of multiple copies of DNA sequences by providing 5' and 3' primers that hybridize to sequences present in a DNA molecule. In one variation of the PCR technology, RT-PCR ("reverse transcriptase-polymerase chain reaction"), may be used to specifically amplify the target mRNA potentially present in the biological sample. Subjecting mRNA to the reverse transcriptase enzyme results in the production of cDNA which is complementary to the base sequences of the mRNA. Large amounts of selected cDNA can then be produced by means of the polymerase chain reaction which relies on the action of heat-stable DNA polymerase produced by Thermus aquaticus for its amplification action.

PCR primers as well as oligonucleotide probes can be designed routinely by those having ordinary skill in the art using cDNA sequence information from the sequence of JAG2. Primers are generally 8-50 nucleotides, preferably 15-30 nucleotides. PCR product, i.e. amplified DNA, may be detected by any of the well known methods.

In another embodiment, the JAG2 protein may be detected by methods directed to the detection of the protein. For example, Western blotting and immunohistochemistry both permit detection of the presence or absence of JAG2. Other immunoassay formats can also be used. For example, as described below, antibody based FACS analysis may also be used for detection of the expression of JAG2 and the quantitation thereof.

In the antibody based detection methods, typically, a first antibody is allowed to bind to the plasma cells in the sample and following removal of non-specific binding, a labeled second antibody or a similar detection molecule is added. The detection of label then provides an indication of the binding of the specific antibody to the plasma cells. If a monoclonal antibody (or an antigen binding fragment thereof) is used, the antibody itself can be labeled thereby eliminating the step of introducing a second antibody. Detectable labels on the antibodies are well known in the art and include labels which have an enzymatic activity that will generate, for example, color development upon incubating with an appropriate chromogenic substrate, or fluorescent labels. Quantification may then be achieved by measuring the degree of color generation using, for example, a visible spectra spectrophotometer or a FACS instrument.

For Western blotting, cell homogenates or purified fractions thereof can be subjected to gel electrophoresis and transferred to blotting filters (such as nitrocellulose filters). The filters are exposed to the antibody and labeled second antibody or other detection methods are used to determine the presence of specific proteins.

For immunofluorescence, tissue sections or cells are typically fixed and exposed to specific antibodies. After removal of non-specific binding, generally by washing with a solution containing a neutral protein such as BSA, a labeled secondary antibody directed against the first antibody is used to indirectly indicate the binding of the specific antibodies to JAG2.

In ELISA assays, an anti-JAG2 antibody is immobilized onto a selected surface, for example, a surface capable of binding proteins such as the wells of a polystyrene microtiter plate. After washing to remove incompletely adsorbed polypeptides, the test sample is introduced. Following formation of specific immunocomplexes between the test sample and the bound polypeptide, the immunocomplex formation may be determined by subjecting the immunocomplex to a second antibody having a detectable label on it.

Polyclonal antibodies directed to JAG2 can be prepared by immunizing a suitable subject with the JAG2. The anti-JAG2 antibody titer in the immunized subject can be monitored over time by standard techniques, such as ELISA using immobilized JAG2. If desired, the antibody molecules directed against JAG2 can be isolated from the mammal (e.g., from the blood) and further purified by well known techniques, such as protein A chromatography to obtain the IgG fraction.

Monoclonal antibodies directed toward JAG2 can also be produced by standard techniques, such as the hybridoma technique originally described by Kohler and Milstein (1975, Nature 256:495-497). Briefly, an immortal cell line (typically a myeloma) is fused to lymphocytes (typically splenocytes) from a mammal immunized with a JAG2, and the culture supernatants of the resulting hybridoma cells are screened to identify a hybridoma producing a monoclonal antibody that binds JAG2 protein. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol. Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind JAG2, e.g., using a standard ELISA assay. Human hybridomas can be prepared in a similar way. Accordingly, the present invention also includes hybridomas secreting monoclonal antibodies specific for the JAG2 protein.

An alternative to preparing monoclonal antibody-secreting hybridomas is to identify and isolate monoclonal antibodies by screening a recombinant combinatorial immunoglobulin library (e.g., an antibody phage display library) with JAG2 protein or fragments thereof.

Antigen binding fragment of antibodies can also be used. These include Fab, F(ab)'$_2$ and Fv. Another example is single chain antibody fragment, i.e., ScFv. These usually comprises the entire antigen binding site and are the smallest antibody fragment that retains specific binding characteristics.

In the diagnosis of plasma cell disorder, a sample is obtained from the bone marrow by methods well known in the art. Once a sample is obtained from the bone marrow, detection of expression of JAG2 and identification of cells as plasma cells can be carried out in the same procedure or in different procedures. Thus, plasma cells can first be isolated by standard techniques such as by using columns having molecules sequestered therein which have specific affinity for plasma cell specific molecules. For example, anti-CD-138 bound magentic beads (Miltenyis) can be used. In another embodiment, the immunofluorescence detection of JAG2 can be combined with an identification of the cells as plasma cells by using a double or triple immunofluorescence procedure. For example, a double fluorescence labeling can be carried out for detection of JAG2 and CD138 (or CD38). In another variation of this embodiment, a triple fluorescence labeling can be carried out for detection of JAG2, CD138 and λ and κ chain of the IgG. Typically, all immunofluorescence methods include controls reacted with either with the isotype control or in the case of polyclonals, only the primary antibodies.

In one embodiment, the level of expression of JAG2 is used to determine the stage of the disease. Thus, based on the level of expression of JAG2, a diagnosis may be made for MGUS, smoldering MM, MM or Plasma cell leukemia. Depending upon the diagnosis, the appropriate therapeutic approach can be selected. For example, more advanced stages such as MM or Plasma cell leukemia typically need more aggressive treatment.

The present invention also provides kits for the detection of plasma cell disorders. The kit may comprise components for the detection of JAG2 mRNA, JAG2 protein or both. For example, the kit may comprises one or more pairs of primers which specifically hybridize to a nucleic acid molecule encoding JAG2, or polyclonal or monoclonal antibodies specific for the JAG2 protein (termed herein as "detection units"), or combinations thereof.

The following examples are presented to illustrate the invention but are not intended to be restrictive in any way.

EXAMPLE 1

This embodiment describes the characterization of the JAG2 transcript in MM cell lines. To determine whether expression or over-expression of JAG2 was present at the transcript level, we performed a series of RT-PCR experiments using primers specific for different regions of the JAG2 cDNA. We used normal B-lymphocytes and an acute leukemia cell line (MUTZ5) as non MM negative controls.

Total RNA was prepared with the ToTALLY™ RNA extraction kit (Ambion, Austin, Tex.) according to manufacturer's instructions. First strand cDNA synthesis (MBI Fermentas, Hanover, Md.) was performed at 42° C. for 1 hour with 1 µg of total RNA. PCR was performed with 100 ng of cDNA in 200 µM for each deoxynucleotide triphosphate and 5 pmole of each JAG2 (forward: 5' GAC GTG CTC TAC CAG TGC AAG AA 3' (SEQ ID NO:1) and reverse: 5' AAC AAC CAC AGG TGC GTC AAC AG 3' (SEQ ID NO:2) or GAPDH primers (Human GAPDH RT-PCR primer, Stratagene, La Jolla, Calif.). The PCR cycle was as follows: 35 cycles at 92° C. for 20", 57° C. for 20", 72° C. for 2 min with a 2-min initial denaturation at 92° C. and a final 10-min elongation step at 72° C. The expected PCR products are either a 912 bp JAG2 fragment or a 525 bp GAPDH fragment. PCR products (10 µl) were electrophoresed on a 1% agarose gel impregnated with ethidium bromide and then photographed. The RT-PCR amplification was repeated up to three times to assure reproducibility of the results.

Figure 3:
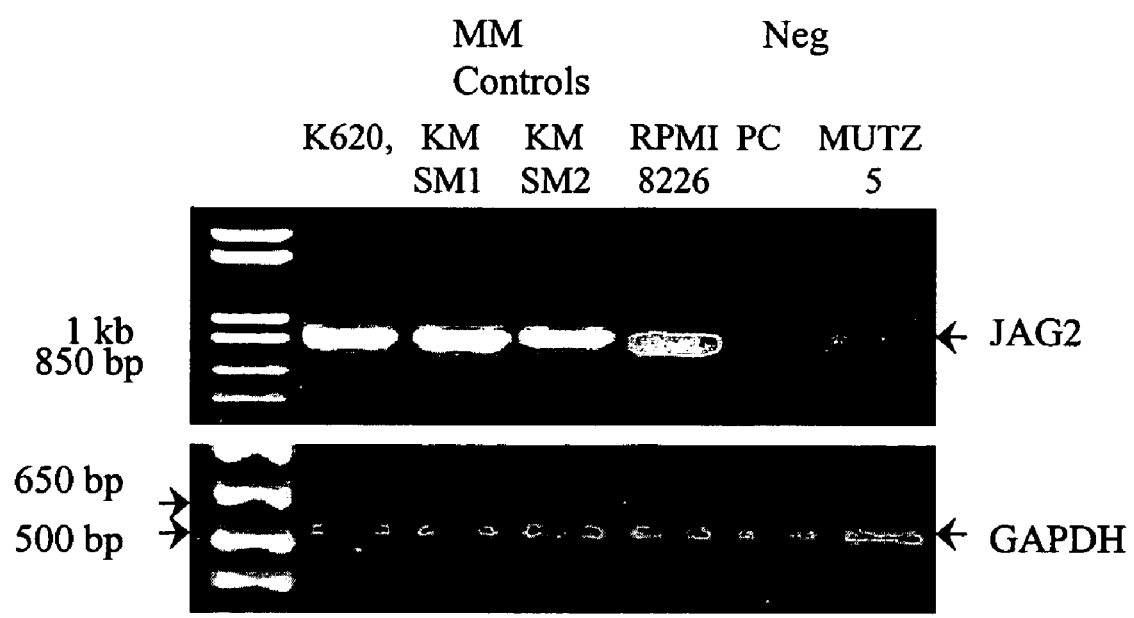
FIG. 3: Representative results of RT-PCR experiments assessing the levels of JAG2 transcripts in JAG2-negative (Normal plasma cells (PC) and MUTZ5-ALL) and—positive (K620, KMSM-1, -2 and RPMI8226) cell lines. GAPDH levels were used to normalize the amount of cDNA present in each tube.

The results are shown in FIG. 3. All MM cell lines tested (K620, KMSM1,-2, RPMI8226, U266) showed JAG2 transcripts as detected by RT-PCR, whereas all the non-MM controls were found to be negative with the signal being barely detectable even by RT-PCR.

EXAMPLE 2

Figure 4A:
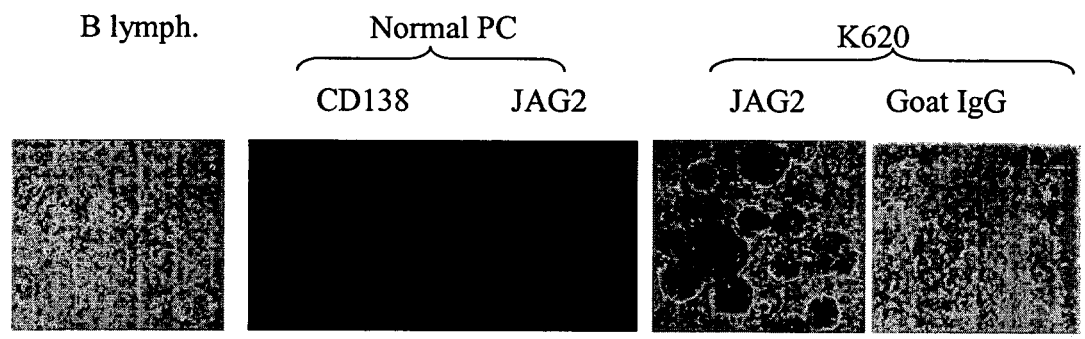
FIGS. 4A and 4B: A) Comparative immunostaining of peripheral blood lymphocytes, normal plasma cells and MM cell lines with the JAG2 (and CD138) antibody; B) Western blot analysis of normal PC, a NIH 3T3 cell line over-expressing JAG2 and 4 MM cell lines (K620, KMSM1,-2, RPMI8226).

This embodiment demonstrates an increased expression of JAG2 protein in MM cell lines. To illustrate this embodiment, we applied a goat polyclonal antibody directed against the carboxy terminus of the JAG2 protein (Santa Cruz Biotechnology) to perform immunohistochemistry (IHC) of 9 MM cell lines. Eight of these cell lines were IL-6 independent while one was IL-6 dependent (IL-6 independence indicates Plasma cell leukemias). Four of the cell lines were tested by Western Blot. As shown in FIG. 4A, comparative immunostaining of peripheral blood lymphocytes, normal plasma cells, and MM cell lines with the JAG2 antibody showed JAG2 expression in the cell lines but not in the controls (B lymphocytes and normal plasma cells are CD138+/JAG2−). Cytospins were prepared from the same cell lines and controls and fixed with acetone for 10 min at room temperature and air-dried. For immunofluorescence, cells were incubated with a goat anti-JAG2 polyclonal antibody (Santa Cruz, Santa Cruz, Calif.) followed by incubation with a FITC-conjugated rabbit anti-goat (Santa Cruz) coupled with a monoclonal PE-conjugated anti-CD138 antibody (Pharmingen-BD, Franklin Lakes, N.J.). Nuclei were counterstained with di-amidino-phenyl-indole (DAPI) (Vectashield, Vector Laboratories, Burlingame, Calif.). For immunocytochemistry, a double stain kit (Dako, Carpinteria, Calif.) was used where the anti-JAG2 antibody was revealed with DAB, whereas the anti-CD138 monoclonal antibody was revealed with Fast Red. No nuclei counterstain was applied.

Figure 4B:
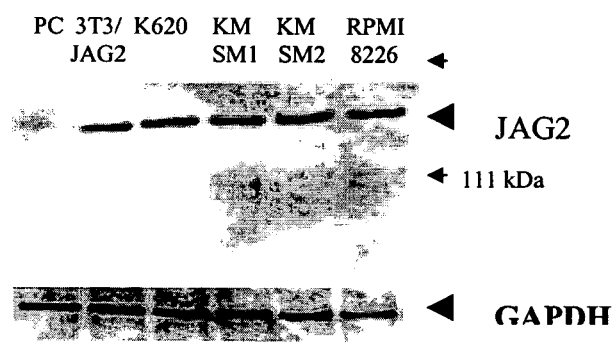

Western blot analysis of 4 MM cell lines (FIG. 4B) confirmed JAG2 expression. An NIH 3T3 cell line constitutively expressing a retrovirally transduced JAG2 (Lane 2) (obtained from Dr Miele, University of Illinois at Chicago) was used as a reference. These representative examples indicate that the expression or over-expression observed in our cell lines is comparable with the ectopic expression directed by a retroviral LTR.

EXAMPLE 3

Figure 5:
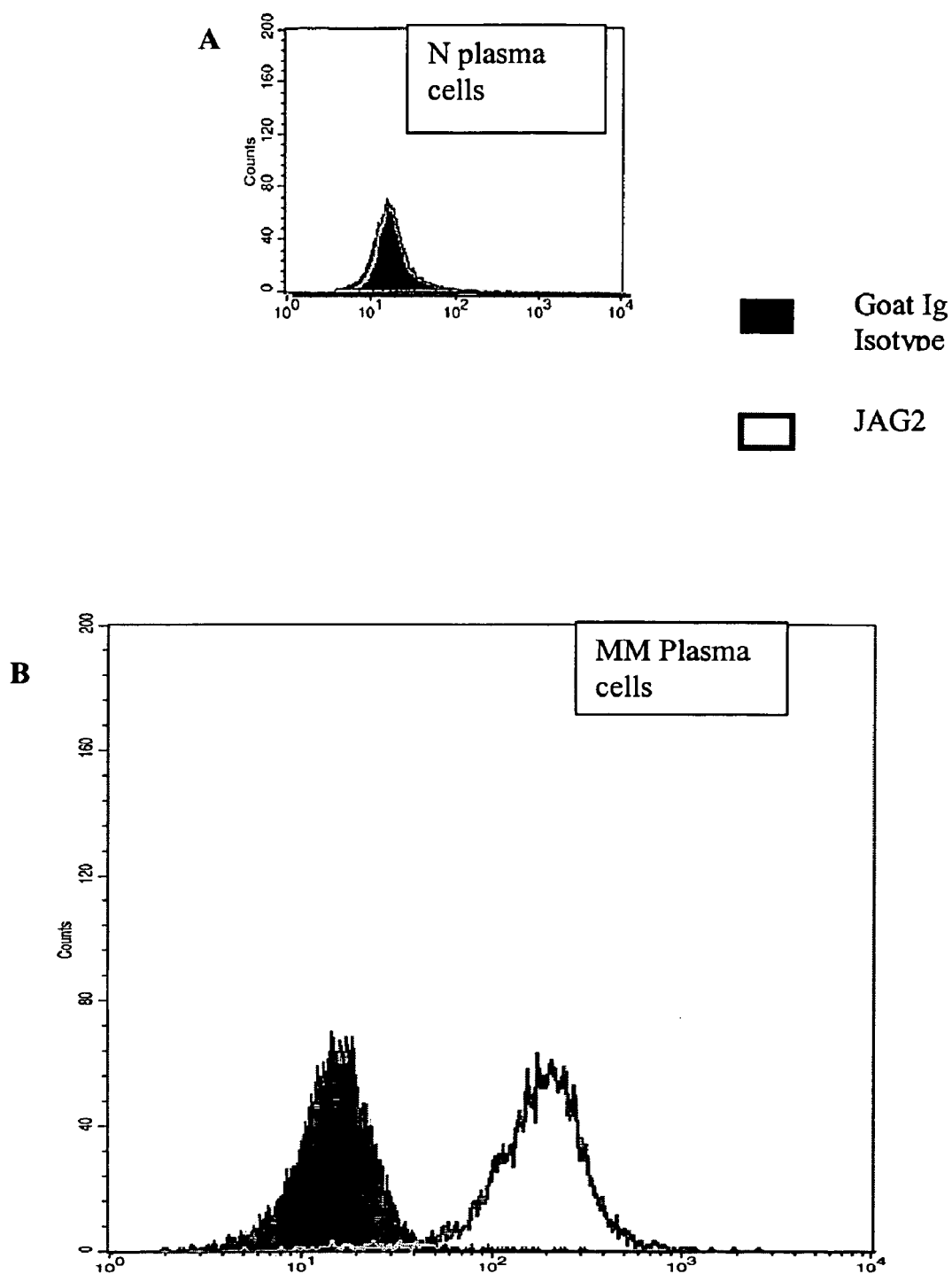
FIG. 5: FACS analysis of A) normal and B) MM plasma cells for JAG2 expression. The JAG2 expression profiles of the CD138+ plasma cells, using either a Goat Ig isotype or anti-JAG2 primary antibodies are shown.

This embodiment describes the determination of JAG2 protein by FACS analysis. To assess JAG2 protein levels in fresh samples, we developed a FACS approach. We were able to quantify JAG2 expression levels in malignant (cell lines) and plasma cells from normal BM as well as from tonsils. We used either a double color approach (anti-CD138-PE and JAG2-FITC) or a single color approach (JAG2-FITC). In the double color approach, cells are fixed with 0.5% foramlin on ice. After washing, 0.5 ml of FITC permeabilizing solution (BD Biosciences, San Jose, Calif.) was added and incubated for 10 min at room temperature. Thereafter, cells were incubated with 1 µg of anti-JAG2 primary antibody followed by 2.5 µg of FITC labeled secondary antibody, followed by an incubation with 1 µg of anti-cd138 PE antibody. In the single color approach, plasma cells are enriched on anti-CD138-bound magnetic beads. We also analyzed plasma cells obtained after culture of B cells with a panel of interleukins (IL-2,-4,-10 and -12) and anti-CD40L. All FACS experiments included controls reacted with either goat Ig isotype- or only anti-JAG2 primary antibodies. As shown in FIG. 5, the normal plasma cells showed a comparable level of JAG2 expression with the goat isotype control antibody whereas all the MM cell lines showed a marked JAG2 expression.

EXAMPLE 4

This embodiment demonstrates that JAG2 protein expression is also observed in primary tumors. To illustrate this embodiment, fresh clinical samples from patients with either MGUS, MM or unrelated disease (for controls) were obtained. The patient samples as well as their principal characteristics regarding their plasma cell status are listed in Table 1.

Figure 6:
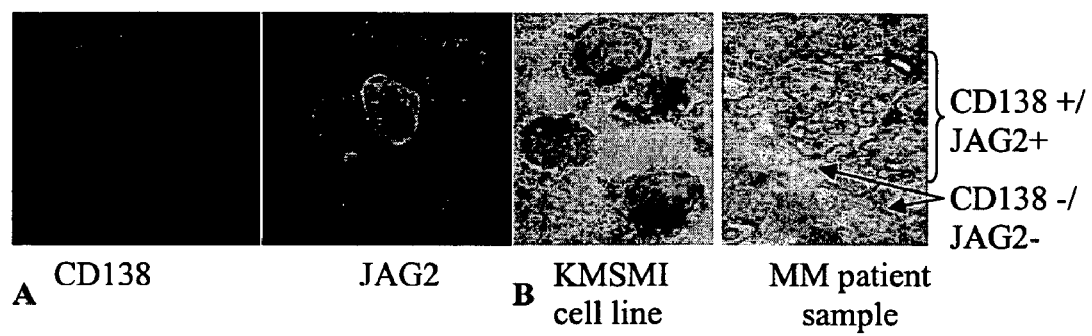
FIG. 6: Immunofluorescence (A) and double-staining immunohistochemistry (B) using anti-JAG2 and anti-CD138 antibodies on patient samples.

Fourteen of these patients were either new patients or patients seen in follow-up examinations, who had either MM, MGUS or smoldering myeloma. Four samples were obtained from non plasma cell disorder patients. The bone marrow (BM) collected was processed to either isolate plasma cells using positive selection with CD138 columns or, when the percentage of plasma cells in the BM was too low, subjected directly to FACS analysis (when the percentage of plasma cells is too low, the loss encountered during the purification process may result in a number of cells too small to analyze and therefore not allow performing an accurate analysis (JAG2+ isotype)). FACS analysis on patient samples was performed using a three-color detection system to ensure an accurate analysis of JAG2 expression in the malignant plasma cells. We used anti-JAG2 (FITC), anti-CD138 (when total BM was used) or anti-CD38 (after CD138+ purification), and anti-kappa or anti-lambda according to the short chain Ig detected in each individual patient. Using this approach, the appropriate cell population for the JAG2 protein level was analyzed. In all cases, immunofluorescence or double stain immunohistochemistry (Dako) was also performed in double color using anti-CD138 (revealed in Rhodamine—red or fast Red-red) and anti-JAG2 (revealed with FITC-green or brown (DAB) (FIG. 6). As shown in Table 1, all the MM related samples showed a marked JAG2 expression whereas the non-MM samples did not. These results are consistent with those obtained with our cell lines. RT-PCR performed on some of the samples (for which we obtained enough cells for both experiments after CD138 selection) showed a similar transcript level increase (data not shown).

TABLE 1

Summary of results obtained with fresh samples by FACS and immunofluorescence analysis in patients with or without plasma cell disorder.

| BM # | BM % cellularity | % plasma cells | Clinical Diagnostic | Monoclonal protein | JAG2 expression |
|---|---|---|---|---|---|
| 9091 | 30 | 4 | No PCD | No MCP | − |
| 4666 | 30 | 3 | No PCD | No MCP | − |
| 4502 | 40 | 7 | Polycythemia Vera | No MCP | − |
| 7812 | 30 | 5 | Hodgkin's | No MCP | − |
| 3201 | — | 1 | Tonsil cells | No PCM | − |
| 4790 | — | 2 | Tonsil cells | No PCM | − |
| 1980 | 30 | 3 | No PCD | Np PCM | − |
| 3205 | 50 | 1 | Low grade NHL | IgA Kappa | − |
| 1409 | 30 | 6 | Breast Ca | No MCP | − |
| 4438 | >90 | 66 | MM | IgG Lambda | + |
| 1906 | 30-40 | 3 | MM in rem. | IgG Kappa | + |
| 6368 | 40 | 14 | MM | IgG Lambda | + |
| 8961 | 45 | 4 | MGUS | IgA Kappa | + |
| 9625 | 40 | 5 | Smoldering MM | IgG Lambda | + |
| 1130 | 30 | 10 | MGUS | IgG Kappa | + |
| 8768 | 30 | 4 | MGUS | IgA Lambda | + |
| 2247 | 70 | 7 | MM treated | IgG Kappa | + |
| 2976 | 60 | 4 | MM treated | IgA Kappa | + |
| 2477 | 50 | 31 | MM | IgG Lambda | + |
| 1291 | 70 | 17 | MM | IgG Kappa | + |
| 4087 | 30 | 31 | MM | IgG Kappa | + |
| 1154 | 30 | 5 | MGUS | IgG Kappa | + |
| 13544 | >90 | 90 | MM | IgG Kappa | + |
| 1332965 | 70 | 25 | MM | IgG Lambda | + |
| 073886 | 30 | 10 | MGUS | IgA Lambda | + |
| 0838 | 80 | 75 | MM | IgA Kappa | + |

EXAMPLE 5

Figure 7:
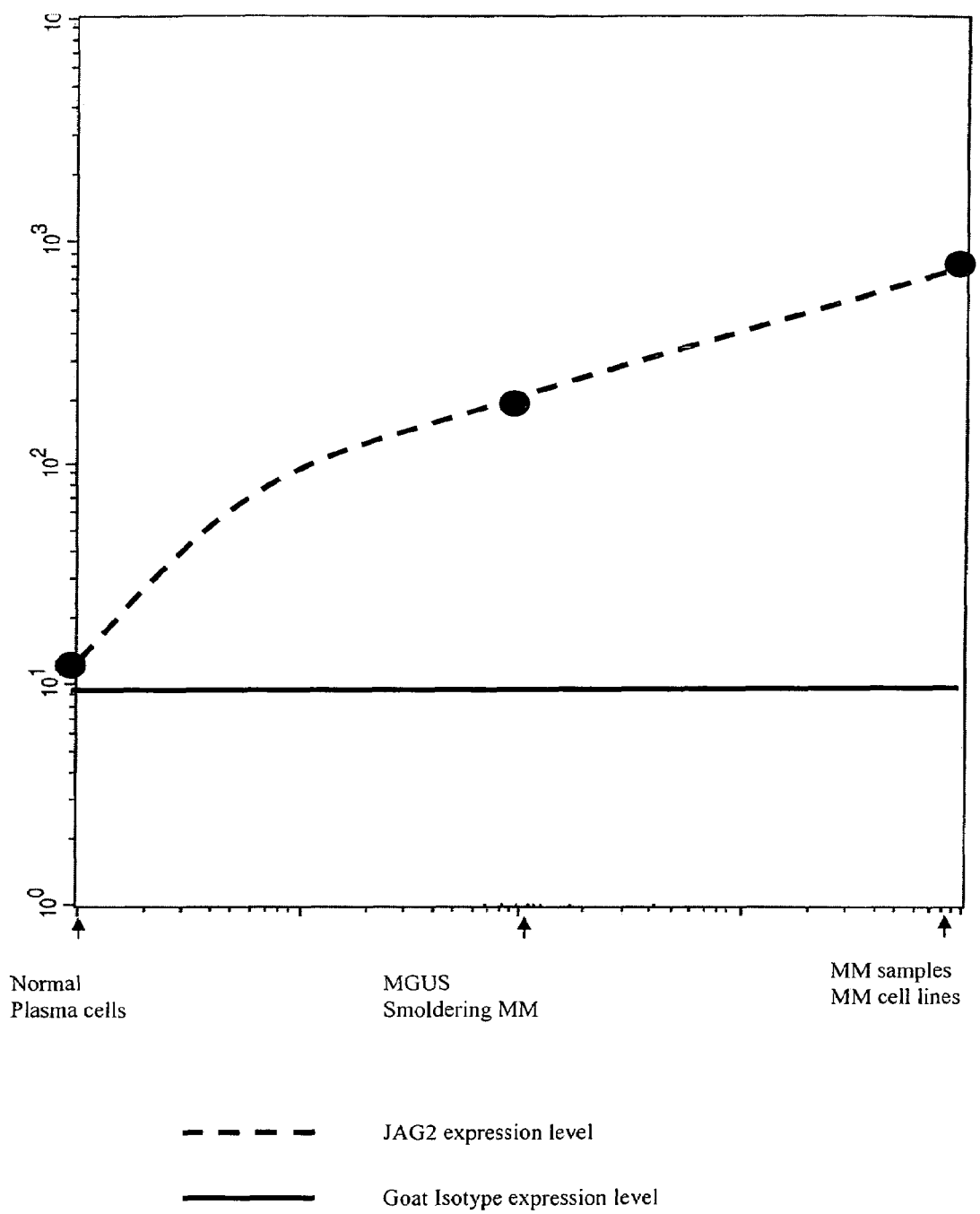
FIG. 7: FACS analysis of the RPMI8226 MM cell line with either secondary antibody alone, M2 or M8 monoclonal antibodies. The hybridoma supernatants were not concentrated in these experiments.

This embodiment demonstrates that monoclonal antibodies can be generated and used for detection of JAG2 protein expression. To illustrate this embodiment, a peptide corresponding to the region of JAG considered to be involved in the binding to JAG2 to NOTCH-1 was synthesized. The sequence of the peptide is CDENYYSATCNKFCRPRND (SEQ ID NO. 3). The peptide was coupled to Keyhole Limpet hemocyanin (KLH). Mice were immunized with the conjugated peptide to generate a polyclonal antibody response. Serum was collected and tested by ELISA. Spleens were removed from the animals and the cells were fused with mouse myeloma cells to create hybridomas. Two monoclonal antibodies M2 (IgG1) and M8 (IgM) were identified. The hybridoma that produces M8 was deposited pursuant to the Budapest Treaty requirements with the American Type Culture Collection (ATCC), 10801 University Boulevard, Manassas, Va. 20110, on Oct. 12, 2006, and has been assigned Patent Deposit Designation PTA-7918. These monoclonals were used for conducting FACS analysis on the MM cells line RPMI18226. The results are shown in FIG. 7. In the top panel, where only the secondary antibody is used, a peak in observed characteristic of this secondary antibody. When either the M2 or the M8 antibodies are used, a shift in the fluorescence peak is observed indicating the specific binding of these antibodies and therefore the expression of JAG2 on these cells.

EXAMPLE 6

Figure 8:
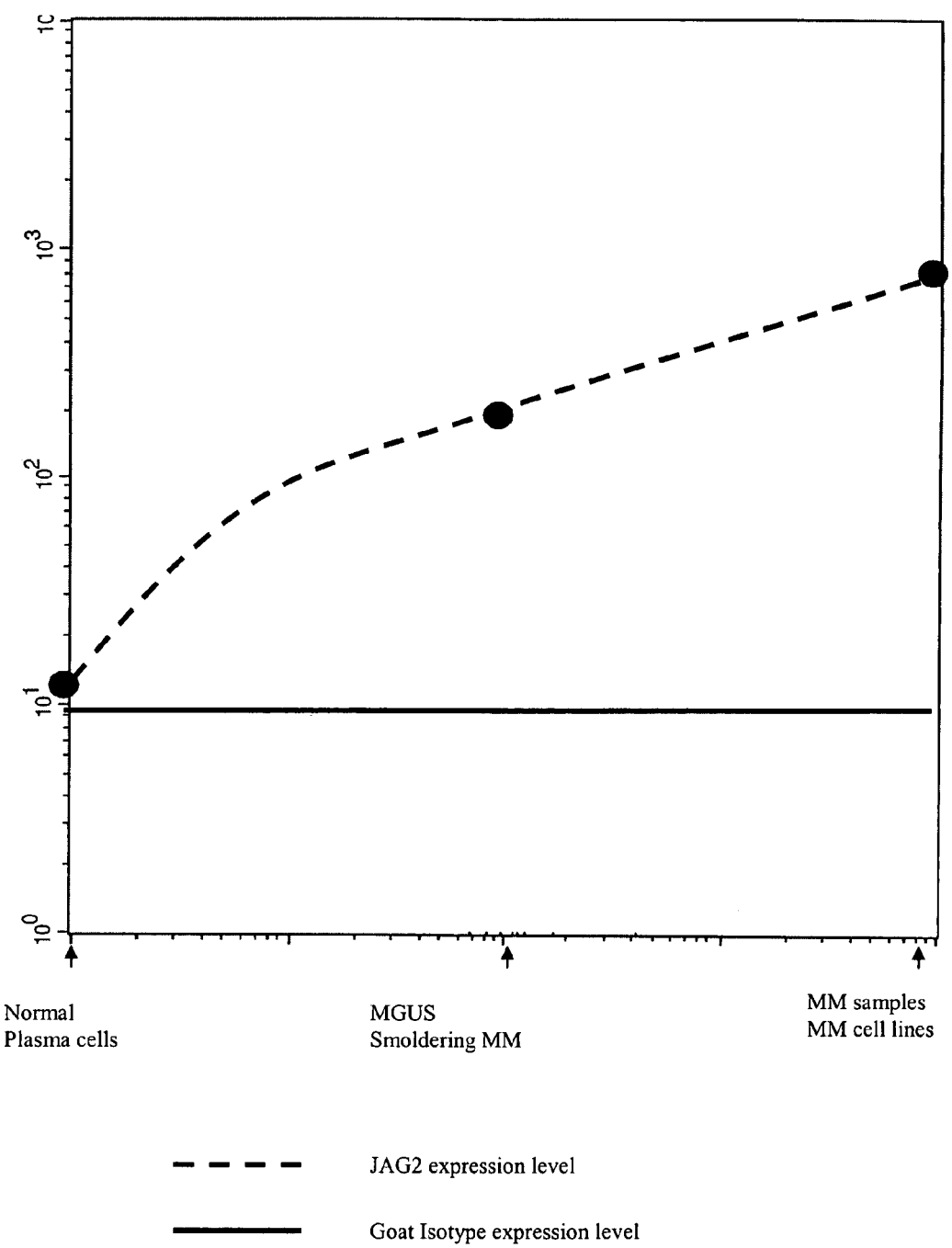
FIG. 8: Schematic representation of the different levels of expression (as compared with the isotype Ig "background") detected in normal plasma cells, MGUS, smoldering MM, MM and cell lines.

This embodiment demonstrates a correlation with JAG2 expression and the stage of the disease in primary tumor samples. To illustrate this embodiment, we assessed JAG2 expression by FACS using a JAG2 polyclonal antibody and a goat isotype as a control. As shown in FIG. 8, there is an increase of JAG2 expression with the stage of the disease, from normal plasma cells (bone marrow, tonsils), MGUS to plasma cell leukemia. Accordingly, determination of the level of JAG2 protein or mRNA can be used to assess the stage of the disease and treatment can be designed accordingly.

EXAMPLE 7

This embodiment demonstrates that JAG2 expression can be used to distinguish plasma cell disorders from other hematologic disorders thereby providing differential diagnosis. This embodiment is illustrated by the following example. In one of the patient samples we studied, there was an increase of plasma cells in the bone marrow and a monoclonal immunoglobin band observed by protein electrophoresis suggested it could be a multiple myeloma. However, when JAG2 expression evaluation was carried out by FACS analysis as described above, there was no increase observed in JAG2 levels. Accordingly, the method of the present invention allowed the differential diagnosis in this case and did not classify it as plasma cell disorder. The patient was then classified as having Non-Hodgkin's lymphoma.

The examples presented herein demonstrate that the oeverexpression of JAG2 can be used to diagnose plasma cell disorders such as MM and MGUS. While specific examples have been presented those skilled in the art will recognize that routing modifications to the embodiments describes herein are possible, which modifications are intended to be within the scope of the invention as encompassed by the claims.

SEQUENCE LISTING

```
<160> NUMBER OF SEQ ID NOS: 3

<210> SEQ ID NO 1
<211> LENGTH: 23
<212> TYPE: DNA
<213> ORGANISM: artificial sequence
<220> FEATURE:
<223> OTHER INFORMATION: PCR forward primer

<400> SEQUENCE: 1
gacgtgctct accagtgcaa gaa                                             23

<210> SEQ ID NO 2
<211> LENGTH: 23
<212> TYPE: DNA
<213> ORGANISM: artificial sequence
<220> FEATURE:
<223> OTHER INFORMATION: PCR reverse primer

<400> SEQUENCE: 2
aacaaccaca ggtgcgtcaa cag                                             23

<210> SEQ ID NO 3
<211> LENGTH: 19
<212> TYPE: PRT
<213> ORGANISM: homo sapiens
<220> FEATURE:
<223> OTHER INFORMATION: peptide corresponding to JAG2

<400> SEQUENCE: 3 cys asp glu asn tyr tyr ser ala thr cys asn lys
                5                   10 phe cys arg pro arg asn asp
        15
```

The invention claimed is:

1. A method for diagnosis of a plasma cell disorder in an individual comprising detecting in a bone marrow sample comprising plasma cells from the individual, wherein the bone marrow sample is processed to enrich for plasma cells:
   a) JAG2 mRNA expression, or
   b) JAG2 protein;
wherein overexpression of JAG2 mRNA relative to a normal control, or overexpression of JAG2 protein relative to a normal control is indicative that the individual has a plasma cell disorder selected from the group consisting of monoclonal gammopathy of unknown significance (MGUS), smoldering myeloma, multiple myeloma and plasma cell leukemia.

2. The method of claim 1, wherein detection of JAG2 mRNA is carried out by a method selected from the group consisting of Northern Blotting, in situ hybridization, PCR based techniques, and a combination thereof.

3. The method of claim 2, wherein the PCR based technique is RT-PCR.

4. The method of claim 3, wherein a pair of primers used for RT-PCR has the sequences of SEQ ID NO:1 and SEQ ID NO:2.

5. The method of claim 1, wherein detection of JAG2 protein is carried out using polyclonal or monoclonal antibodies, or antigen-binding fragments thereof specific for the JAG2 protein.

6. The method of claim 5, wherein the detection of JAG2 protein is carried out by using FACS analysis using a monoclonal antibody.

7. The method of claim 5, wherein the detection of JAG2 protein is carried out by using a polyclonal antibody.

8. The method of claim 5, wherein the detection of JAG2 protein is carried out by using a monoclonal antibody.

9. The method of claim 5, wherein the monoclonal antibody is specific against the peptide of SEQ ID NO:3.

10. The method of claim 9, wherein the monoclonal antibody is monoclonal antibody M8.

11. The method of claim 1, wherein the bone marrow sample is enriched in plasma cells by selective adsorption by plasma cell specific antibodies.

12. The method of claim 11, wherein the plasma cell specific antibodies comprise monoclonal antibody M8.

13. The method of claim 1, wherein the level of expression of JAG2 mRNA or the level of JAG protein in the bone marrow sample is compared to a negative control.

14. A method for determining a plasma cell disorder in an individual comprising the step of detecting in a bone marrow sample from the individual comprising plasma cells:
   JAG2 protein expression,
wherein expression of JAG2 protein of about 10 times greater than the level of JAG2 protein expression of a normal control is indicative of smoldering myeloma or MGUS, and wherein expression of JAG2 protein of about 100 times greater than the level of JAG2 protein expression of the normal control is indicative of multiple myeloma.

15. The method of claim 14, wherein detection of JAG2 protein is carried out using polyclonal or monoclonal antibodies, or antigen-binding fragments thereof specific for the JAG2 protein.

16. The method of claim 15, wherein the detection of JAG2 protein is carried out by using FACS analysis using a monoclonal antibody.

17. The method of claim 16, wherein the monoclonal antibody is specific for the peptide of SEQ ID NO:3.

18. A kit for diagnosis of plasma cell disorder in sample comprising plasma cells, said kit comprising a pair of primers which specifically hybridize to a nucleic acid molecule encoding JAG2, and reagents for performing RT-PCR, wherein the sequences of the primer pair are SEQ ID NO: 1 and SEQ ID NO:2.

19. A kit useful for diagnosis of plasma cell disorder comprising a monoclonal antibody specific for the JAG2 protein, antigen binding fragments of the monoclonal antibody and combinations thereof; and regents for performing immunological detection, wherein the monoclonal antibody is reactive against the peptide of SEQ ID NO:3.

20. The kit of claim 19, wherein the monoclonal antibody has a detectable label thereon.

21. The kit of claim 19, wherein the monoclonal antibody is monoclonal antibody is M8.

22. A monoclonal antibody specific for JAG2 protein, wherein the monoclonal antibody thereby binds to plasma cells which express the JAG2 protein on the surface, and wherein the monoclonal antibody is reactive against the peptide of SEQ ID NO:3.

* * * * *